(12) United States Patent
Zhang et al.

(10) Patent No.: US 10,398,487 B2
(45) Date of Patent: Sep. 3, 2019

(54) THREE-DIMENTIONAL REPOSITOR FOR CLAVICLAR FRACTURE

(71) Applicant: Yingze Zhang, Shijiazhuang, Hebei Province (CN)

(72) Inventors: Yingze Zhang, Shijiazhuang (CN); Wei Chen, Shijiazhuang (CN); Juan Wang, Shijiazhuang (CN); Qi Zhang, Shijiazhuang (CN)

(73) Assignee: Yingze Zhang, Shijiazhuang, Hebei (CN)

( * ) Notice: Subject to any disclaimer, the term of this patent is extended or adjusted under 35 U.S.C. 154(b) by 548 days.

(21) Appl. No.: 15/104,595

(22) PCT Filed: Feb. 25, 2015

(86) PCT No.: PCT/CN2015/073270
§ 371 (c)(1),
(2) Date: Jun. 15, 2016

(87) PCT Pub. No.: WO2015/154593
PCT Pub. Date: Oct. 15, 2015

(65) Prior Publication Data
US 2016/0310195 A1  Oct. 27, 2016

(30) Foreign Application Priority Data
Apr. 9, 2014 (CN) .......................... 2014 1 0139857

(51) Int. Cl.
*A61B 17/88* (2006.01)
*A61B 17/60* (2006.01)
(Continued)

(52) U.S. Cl.
CPC .......... *A61B 17/8866* (2013.01); *A61B 17/60* (2013.01); *A61B 2017/00367* (2013.01); *A61B 2017/564* (2013.01); *A61B 2017/681* (2013.01)

(58) Field of Classification Search
CPC .......... A61B 17/62; A61B 17/64; A61B 17/66
See application file for complete search history.

(56) References Cited

U.S. PATENT DOCUMENTS 2,055,024 A * 9/1936 Bittner, Jr. ............. A61B 17/62
606/56
7,465,303 B2   12/2008 Riccione et al.
(Continued)

FOREIGN PATENT DOCUMENTS

CN      201441444 U      4/2010
CN      102247198 A     11/2011
(Continued)

OTHER PUBLICATIONS

International Search Report for International Application No. PCT/CN2015/073270, dated May 22, 2015.
The CN1OA issued by CNIPA dated Aug. 28, 2014.

*Primary Examiner* — Samuel S Hanna
(74) *Attorney, Agent, or Firm* — Yunling Ren (57) ABSTRACT

A three-dimensional repositor for claviclar fracture includes two supporting rods, which independently comprise a straight part and a curved part separately, and are rotatably connected each other through a rotation shaft at the two ends of the curved parts; the two supporting rods are each provided with opposite locating holes correspondingly and perpendicularly downwards, which have a diameter matching with a diameter of either a locating screw or a Kirschner wire; and at least one first reduction device, each of which includes two pillars perpendicular to the straight part of the two supporting rods respectively; and a cross bar moveably disposed on top ends of the two pillars at both ends respectively, and comprising a plurality of reduction holes having a diameter matching with a diameter of the Kirschner wire.

3 Claims, 6 Drawing Sheets

(51) Int. Cl.
  *A61B 17/00* (2006.01)
  *A61B 17/56* (2006.01)
  *A61B 17/68* (2006.01)

(56) References Cited

U.S. PATENT DOCUMENTS

| | | | |
|---|---|---|---|
| 2005/0149018 A1* | 7/2005 | Cooper | A61B 17/6425 |
| | | | 606/54 |
| 2005/0149039 A1* | 7/2005 | Haines | A61B 17/155 |
| | | | 606/87 |
| 2005/0251135 A1 | 11/2005 | Riccione et al. | |
| 2013/0204248 A1* | 8/2013 | Singh | A61B 17/62 |
| | | | 606/56 |

FOREIGN PATENT DOCUMENTS

| | | | | |
|---|---|---|---|---|
| CN | 202051802 U | | 11/2011 | |
| CN | 102551848 A | | 7/2012 | |
| CN | 102551854 | * | 7/2012 | A61B 17/68 |
| CN | 102551854 A | | 7/2012 | |
| CN | 202654206 U | | 1/2013 | |
| CN | 103445836 A | | 12/2013 | |
| CN | 103892896 A | | 7/2014 | |
| CN | 203749535 U | | 8/2014 | |
| RU | 2217090 C2 | | 11/2003 | |

\* cited by examiner

THREE-DIMENTIONAL REPOSITOR FOR CLAVICLAR FRACTURE

CROSS REFERENCE

This application is an US national phase of International Application No. PCT/CN2015/073270, filed on Feb. 25, 2015, which is based upon and claims priority to Chinese Patent Application No. 201410139857.1, filed on Apr. 9, 2014, and the entire contents thereof are incorporated herein by reference.

TECHNICAL FIELD

The present disclosure relates to a field of medical apparatus for orthopedic operation, particularly, relates to a repositor for treatment for claviclar fracture and dislocation of acromioclavicular joint.

BACKGROUND

During orthopedic operation, it is necessary to master the reduction and fixation for the claviclar fracture and dislocation of acromioclavicular joint. The claviclar fracture is mainly caused by direct violence such as fall damage, which is accounted for 2.6%-5% of the total, and 44% of shoulder girdle damage. The claviclar fracture occurred at the middle ⅓ shaft of the clavicle is common, which is accounted for 69%-82% of claviclar fracture. The ends of the fractured clavicle will cause varying degrees of displacement upwards, forwards or backwards. The dislocation of acromioclavicular joint is accounted for 12% of the total dislocation. Clavicle plays an important function for acromioclavicular joint movement. Clinical dislocation of acromioclavicular joint is commonly caused by acromion strain, or indirect damage, such as outside force transferred upwards along humerus when the people falls down on hand or elbow. Varying degrees of upwards or forwards displacement of the clavicle compared with the humerus may cause varying degrees of damage to neighboring ligament, thus resulting in problems to shoulder joint. Internal fixation therapy is adopted for treating claviclar fracture, which includes fixation with Kirschner wire, plate, shape memory alloy embracing clavicle fixator or the like. Operations for dislocation of acromioclavicular joint are various, such as steinmann pin tension band fixation, hook plate fixation, wire fixation or the like. No matter which internal fixation is applied, the major premise of satisfactory treatment for claviclar fracture and dislocation of acromioclavicular joint is good, effective, and continuous reduction until the fixation is completed. The fractured ends of the clavicles will overlap. Conventional reduction method is: kneeing to back, holding and twisting shoulder backwards to pull and align the overlapped fracture fragments. However, the above mentioned method is time-consuming and laborious, is difficult to achieve accurate reduction for claviclar fracture, and is unable to be completed by one person.

China patent No. 201210005268.5 discloses a repositor for the treatment for claviclar fracture and dislocation of acromioclavicular joint, which adopts a bed board for raising the back of the patient and a fasten belt at both sides for fixing, such that it could effectively solve a problem of how to reduce the fractured clavicle and acromioclavicular joint. However, the above apparatus, raising the back of the patient, could not be applicability for a patient with backache, thus being limited in use. Therefore, both medical staff and patient hope that a new surgical instrument and method would be developed, which could perform an accurate and fast reduction for the claviclar fracture so as to obtain a better effect, relive patient's pain and improve operation efficiency.

The foresaid information as disclosed in the background part only serves to enhance understanding of the background of the disclosure, thereby it may not contain ordinary skill information that has been well known.

SUMMARY

The technical problem to be solved by the present disclosure is to provide a three-dimensional repositor for claviclar fracture, which could perform a fast reduction for the claviclar fracture and dislocation of acromioclavicular joint, is easy to use, effectively maintain reduction until internal fixation is completed.

Additional aspects and advantages of the disclosure will be in part set forth in the description below, and in part will become obvious from the description, or may be learned from practice of the present disclosure.

In order to achieve the above objectives, the following technical solution is adopted by the present disclosure:

In one aspect, the present disclosure provides a three-dimensional repositor for claviclar fracture includes two supporting rods, which independently includes a straight part and a curved part separately, and are rotatably connected each other through a rotation shaft at the two ends of the curved parts; the two supporting rods are each provided with opposite locating holes correspondingly and perpendicularly downwards, which have a diameter matching with a diameter of either a locating screw or a Kirschner wire; and at least one first reduction device, each of which includes two pillars perpendicular to the straight part of the two supporting rods respectively; and a cross bar moveably disposed on top ends of the two pillars at both ends respectively, and including a plurality of reduction holes having a diameter matching with a diameter of the Kirschner wire.

In an embodiment of the present disclosure, wherein the straight part of the supporting rod has a bending portion bending upwards, the locating hole is provided at a turning portion of the bending portion, which is located at the lowest point of the supporting rod; and the first reduction device is located at the bending portion.

In an embodiment of the present disclosure, wherein further includes a position block, the locating hole is disposed on the position block, and a universal wheel structure is disposed at one side or both sides of the position block, which connects the bending part or the supporting rod respectively.

In an embodiment of the present disclosure, wherein a groove is provided on the supporting rod in a length direction of the supporting rod, and the lower end of the pillar is slidably mounted in the groove.

In an embodiment of the present disclosure, wherein a rotation hole or a chip is provided at the pillar, and a rotation shaft of cross bar is provided at both ends of the cross bar respectively, which passes through the rotation hole of the pillar or is received in the chip of the pillar.

In an embodiment of the present disclosure, wherein a screw hole is provided on the cross bar and communicated with the reduction hole, in which a screw is received for tightly pressing the Kirschner wire.

In an embodiment of the present disclosure, wherein two first reduction devices are mounted at both sides of the locating hole respectively.

In an embodiment of the present disclosure, wherein the cross bar is perpendicular to the straight part of the supporting rod.

In an embodiment of the present disclosure, wherein a shaft hole is provided on the supporting rod for receiving the rotation shaft, which is a circle hole or a long hole.

In an embodiment of the present disclosure, wherein upper surfaces of the straight parts of the two supporting rods are in the same plane.

In an embodiment of the present disclosure, wherein further including a second reduction device, which includes two extension rods formed by bending outwards and extending from the ends of the curved parts of the two supporting rods, and coplanar at the upper surfaces; and a screw rod matched with one of the extension rods via screw thread, one end of the screw rod movably connects to the other one of the extension rods, and the other end is provided with a crank.

In an embodiment of the present disclosure, wherein further including a second reduction device, which includes a sleeve having opening at both ends and a notch at middle; a cam rotatably mounted at the center of the sleeve and provided with a rotation handle thereon; two pushing rods, one end of which connects to the supporting rod and the other end of which inserts into the sleeve and contacts against the cam, the pushing rods could stretch out or draw back along with the rotation of the cam; and a pushing rod locking device mounted on either the sleeve or the pushing rods for locking the sleeve and the pushing rods.

In an embodiment of the present disclosure, wherein the cam is oval.

In an embodiment of the present disclosure, wherein a stretched spring is connected between the two supporting rods.

In an embodiment of the present disclosure, wherein a slot is provided on the pushing rods, the pushing rod locking device is a pawl with function of uni-directional brake mounted on the sleeve and be capable of inserting into the sleeve and blocking the slot uni-directionally.

According to the above technical solutions, the present disclosure has advantageous technical effects as follow:

During operation with the three-dimensional repositor for claviclar fracture of the present disclosure, the patient is allowed to lie on her or his back, locating the locating holes at the supporting rods corresponding to two ends of the fractured clavicle respectively, fixing the locating hole by reduction screw, then the dislocated clavicle could be moved upwards, downwards, leftwards or rightwards to be reduced with the cooperation of the cross bar of the first reduction device and a plurality of Kirschner wires.

Further, if the second reduction device is provided, pulling the clavicle with longitudinal dislocation sideward by the second reduction device, then passing the Kirschner wire through the reduction hole of the cross bar to press or raise the fractured clavicle. The distance between two ends of the pulled clavicle could be controlled by the second reduction device, and maintained to reach a stable reduction condition by cooperation of the second reduction device and screw at the cross bar until internal fixation is completed.

The present disclosure is smartly designed with simple structure, convenient to use, thus the effect of stable three-dimensional reduction for the claviclar fracture is achieved, which relieves patient's pain and reduces difficulty for operation, produces unexpected technical effect. The present disclosure is welcomed by medical staff and patient, and is worthy of popularization.

The above and other features and advantages of the present disclosure will become more apparent from the detailed description of exemplary embodiments thereof with reference to accompany drawings.

Reference numerals in the above drawings are as follows: supporting rod 1, rotation shaft 2, locating hole 3, locating screw 4, pillar 5, cross bar 6, rotation shaft of cross bar 7, reduction hole 8, Kirschner wire 9, pushing rod 10, sleeve 11, cam 12, stretched spring 13, rotation handle 14, slot 15, pawl 16, extension rod 17, screw rod 18, screw hole 19, crank 20, groove 21, screw hole 22, universal wheel structure 23.

DETAILED DESCRIPTION

Specific embodiments in this disclosure have been shown by examples in the foregoing drawings and are hereinafter described in detail. The figures and written description are not intended to limit the scope of the inventive concepts in any manner. Rather, they are provided to illustrate the inventive concepts to a person skilled in the art by reference to particular embodiments. The same or similar features employ identical reference numerals, and the detailed description thereof is omitted.

Embodiment 1

Figure 1:
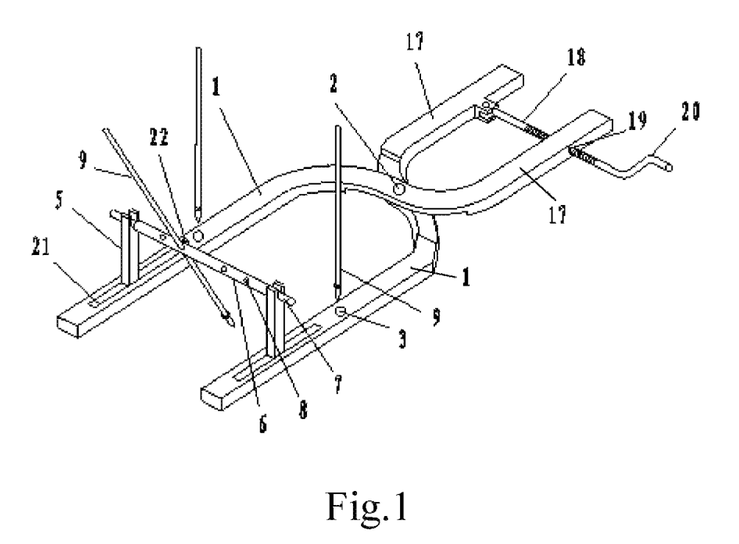
FIG. 1 is a perspective schematic view according to the first embodiment of the three-dimensional repositor for claviclar fracture of the present disclosure.

As shown in FIG. 1, according to the first embodiment of the three-dimensional repositor for claviclar fracture of the present disclosure, it includes two supporting rods 1, and a first reduction device and a second reduction device mounted at the two supporting rods 1.

Figure 4:
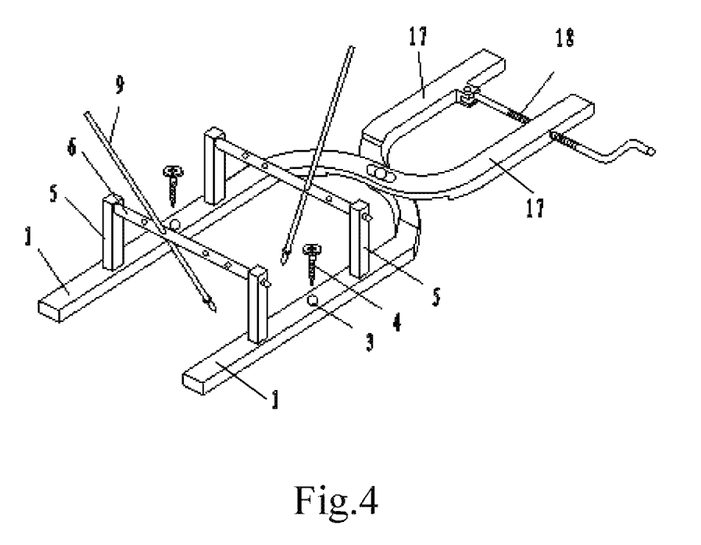
FIG. 4 is a perspective schematic view according to the fourth embodiment of the three-dimensional repositor for claviclar fracture of the present disclosure.

The supporting rod 1 has a straight part and a curved part. The two supporting rods 1 are connected together at one end of the curved part through a rotation shaft 2. The straight parts of the two supporting rods 1 may be in parallel with each other. Shaft holes provided at two supporting rods 1 are of circle. The rotation shaft 2 is cylindrical which passes through the shaft holes so as to connect the two supporting rods 1, and the upper surfaces of straight parts of two supporting rods 1 connected by the rotation shaft 2 may be in the same plane. A locating hole 3 is provided at each supporting rods 1 perpendicularly and downwards, which has a diameter matching with a diameter of a Kirschner wire 9 or a locating screw 4 (as shown in FIG. 4).

The reduction operation includes longitudinal reduction and dislocated reduction in direction of top, bottom, left and right. The longitudinal reduction is performed by the cooperation of supporting rods 1 and the second reduction device, and the dislocated reduction in direction of top, bottom, left and right is performed by the cooperation of supporting rods 1, the first reduction device and the Kirschner wire 9.

As shown in FIG. 1, the first reduction device includes two pillars 5 mounted on the supporting rods 1 respectively and a cross bar 6 moveably located on top ends of the two pillars 5. The pillars 5 and cross bar 6 are perpendicular to the straight part of the supporting rod 1. The pillar 5 is in a height of 3-10 cm. Either a rotation hole or a chip is provided at upper end of the pillar 5, and a rotation shaft of cross bar 7 is provided at both ends of the cross bar 6, which passes through the rotation hole or is received in the chip. There is a sliding contact between the rotation shaft of cross bar 7 and the rotation hole or chip. When the supporting rod 1 moves sideward, the cross bar 6 and the upper end of the pillar 5 keep connecting. A plurality of reduction holes 8 are provided at the cross bar 6, which have a diameter matching with a diameter of the Kirschner wire 9. During operation, the Kirschner wire 9 connects to the fractured clavicle via the reduction hole 8 at the cross bar 6, and the Kirschner wire 9 might be pushed or pulled as needed so as to move the fractured clavicle upwards or downwards to achieve the reduction. The cross bar 6 might be rotated by rotating the rotation shaft of cross bar 7, such that the angle of the reduction hole 8 may be adjusted so as to rotate the Kirschner wire 9 to an optimum angle.

As shown in FIG. 1, in order to adjust the first reduction device to an optimum position, a groove 21 may be provided on the supporting rod 1 in a length direction of the supporting rod 1. The lower end of the pillar 5 is slidably engaged in the groove 21. During reduction operation, the pillar 5 may be pushed along the groove 21 to an optimum position.

As shown in FIG. 1, the Kirschner wire 9 passing through the reduction hole 8 of the cross bar 6 needs to be positioned and locked after the reduction operation, to this end, a screw hole 22 is drilled at a side of the reduction hole 8 on the cross bar 6 and communicated with the reduction hole 8. The Kirschner wire 9 in the reduction hole 8 is tightly pressed by a screw in the screw hole 22 so as to be positioned and locked. The structure for locking the Kirschner wire 9 is not limited thereto, any other structure capable of locking is adaptable for the disclosure.

As shown in FIG. 1, the second reduction device includes two extension rods 17 and a screw rod 18. The two extension rods 17 are formed by bending outwards and extending from the ends of the curved parts of the two supporting rods 1, which are parallel with each other, and are coplanar at the upper surfaces. The two supporting rods 1 with the two extension rod 17 are configured in a scissor-shape. The screw rod 18 is disposed between the two extension rods 17. In detail, one of the extension rods 17 is provided with a mounting seat, on which one end of the screw rod 18 is rotatably mounted through a rotation shaft; the other extension rod 17 is provided with a screw hole 19 matching with the screw rod 18. The screw rod 18 passes through the screw hole 19 and has a crank 20 at the other end. During operation, the screw rod 18 may push the two extension rods 17 open by rotating the crank 20 so as to open the supporting rods 1, such that the clavicle with longitudinal dislocation may be pulled to be repsited. Self-lock may be achieved after rotation by the crew rod 18 with self-lock function.

In the first embodiment, the screw rod 18 may be positioned at lower part of the two supporting rods 1 without using the extension rod 17 of the second reduction device. However, the above structure may be inconvenient for operation, since the lower part of the two supporting rods 1 is in the patient's body.

The second reduction device may also adopt other similar structures, such as traction bow which has a complicated structure and not as easy as the foregoing two structures for manufacture and use.

Embodiment 2

Figure 2:
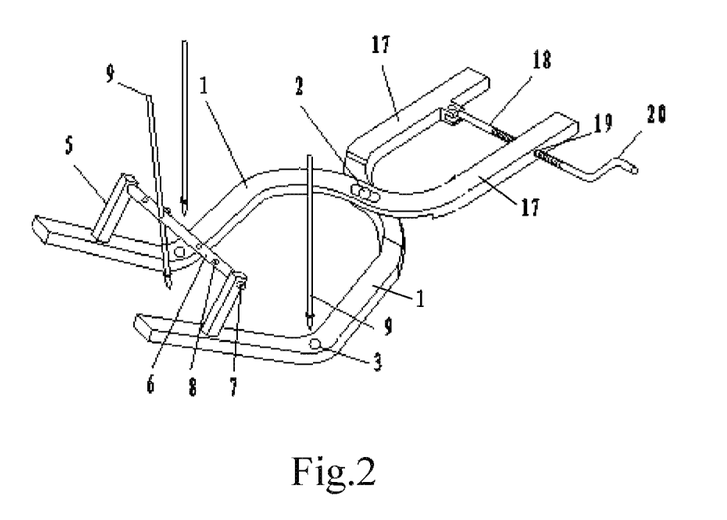
FIG. 2 is a perspective schematic view according to the second embodiment of the three-dimensional repositor for claviclar fracture of the present disclosure.

As shown in FIG. 2, the second embodiment of the three-dimensional repositor for claviclar fracture of the present disclosure is different from that in the first embodiment as described below.

One of the shaft holes on the two supporting rods 1 for receiving the rotation shaft 2 is a long hole so as to adjust a basic distance between the two supporting rods 1. In other embodiments, both shaft holes may be long holes.

The straight part of the supporting rod 1 has a bending portion bending upwards. The locating hole 3 of the supporting rod is provided at a turning portion of the bending portion, which is located at the lowest point of the supporting rod 1. The first reduction device is located at the bending portion of the supporting rod 1. The bending portion of the supporting rod 1 has an advantageous of avoiding affecting to a wound at breast or chest.

Other parts of the second embodiment are the same as that of the first embodiment mentioned above and the detailed description is omitted herein.

Embodiment 3

Figure 3:
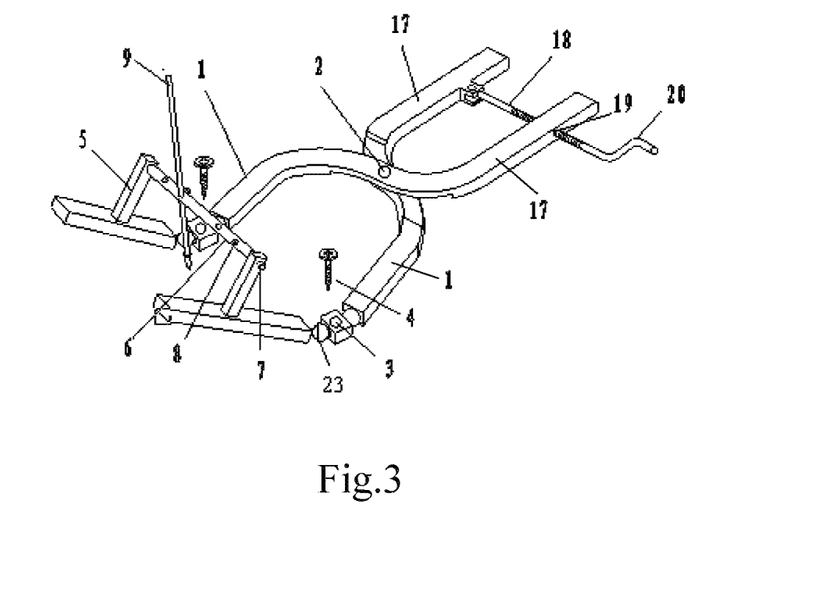
FIG. 3 is a perspective schematic view according to the third embodiment of the three-dimensional repositor for claviclar fracture of the present disclosure.

As shown in FIG. 3, the third embodiment of the three-dimensional repositor for claviclar fracture of the present disclosure is different from that in the second embodiment as described below.

The angle of the bending part of the supporting rod 1 may be adjusted. In detail, the third embodiment is provided with a position block. The locating hole 3 is disposed in the position block. A universal wheel structure 23 is disposed at one side or both sides of the position block, which connects the bending part with the supporting rod 1 respectively. During operation, the angle of the bending part may be adjusted by the universal wheel structure 23 until a proper angle achieved, and then the universal wheel structure 23 may be locked.

Other parts of the third embodiment are the same as that of the second embodiment mentioned above and the detailed description is omitted herein.

Embodiment 4

As shown in FIG. 4, the fourth embodiment of the three-dimensional repositor for claviclar fracture of the present disclosure is different from that in the first embodiment as described below.

The fourth embodiment is provided with two first reduction devices at both sides of the locating hole 3 respectively. Two cross bars 6 of the two first reduction devices may be parallel with each other. During operation, any one of the first reduction devices with different positions may be chosen, such that the Kirschner wire 9 could be inserted in different directions, thus reaching a better reduction effect.

Other parts of the fourth embodiment are the same as that of the first embodiment mentioned above and the detailed description is omitted herein.

Embodiment 5

Figure 5:
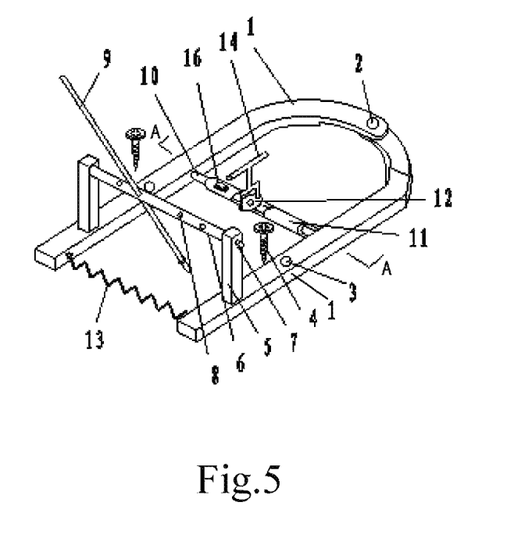
FIG. 5 is a perspective schematic view according to the fifth embodiment of the three-dimensional repositor for claviclar fracture of the present disclosure.

As shown in FIG. 5, the fifth embodiment of the three-dimensional repositor for claviclar fracture of the present disclosure is different from that in the first embodiment as described below.

None of the supporting rods 1 is provided with an extension rod 17.

The second reduction device includes two pushing rods 10, a sleeve 11, a cam 12 and a stretched spring 13. The sleeve 11 has opening at both ends and a notch at middle. One end of the pushing rod 10 movably connects to an inner wall of the supporting rod 1, and the other end inserts into the sleeve 11 and contacts against the cam 12. The cam 12 is oval which is rotatably mounted at the center of the sleeve 11 at the center via a rotatable shaft, and the cam 12 connects to a rotation handle 14 at an upper part of the center axis. During operation, the cam 12 is rotated by rotating the rotation handle 14. The distance between any point at edge of the oval cam 12 and center axis is different, so that the movement distance of the pushed part of the pushing rod 10 is different when rotating the cam 12, thus width of the two supporting rod 1 pushed by the pushing rod 10 is accordingly different. The two supporting rods 1 move outwards the fractured clavicle at both sides, such that the clavicle with longitudinal dislocation may be pulled to be reposited. The operator may rotate the cam 12 as required so as to pull with different distance. The difference between the distance from the center of the cam 12 to the distal end and to the proximal end is 15-30 mm, i.e., the maximum distance of the pushing rod 10 pushed by the cam 12 is 60 mm which is enough for longitudinally pulling the dislocated clavicle.

Figure 6:
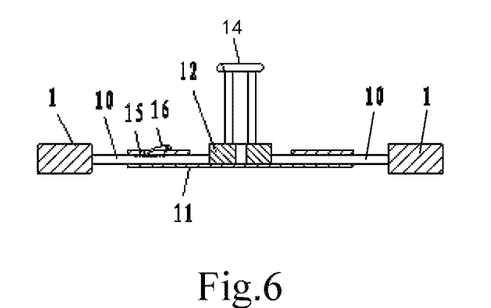
FIG. 6 is a section view along line A-A of FIG. 5.

As shown in FIGS. 5 and 6, in order to reach self-lock of the cam 12 after rotation, a slot 15 is sunken downwards at periphery of the pushing rod 10, and is right triangle with a right-angle side perpendicular to an axis of the pushing rod 10, and a hypotenuse connecting between two right-angle sides. A pawl 16 with function of uni-directional brake is provided at wall of the sleeve, which is cooperated with the slot 15. when the pushing rod 10 moves outwards, a front end of the pawl 16 moves along the hypotenuse of the slot 15 without interfering the movement of the slot 15; when the pushing rod 10 is pushed in place, the front end of the pawl 16 contacts against the rear of the right-angle side of the slot 15. Because the pawl 16 may not be rotate backwards, the pushing rod 10 is blocked without moving, therefore, the self-lock is achieved.

As shown in FIGS. 5 and 6, the stretched spring 13 is connected between the ends of the two supporting rods 1, which may maintain a tight contact between the pushing rod 10 and the cam 12, and insure the two supporting rods 1 are not loose.

The present disclosure may perform reduction for dislocated clavicle by pull and alignment. During reduction, locating the locating holes 3 at the supporting rods 1 corresponding to two ends of the fractured clavicle respectively, fixing the locating hole 3 by locating screw 4, pulling the clavicle with longitudinal dislocation sideward by the second reduction device, then the fractured clavicle may be pressed or raised by the Kirschner wire 9 through the reduction hole 8 of the cross bar 6, and performing reduction for dislocated clavicle by X-ray inspection and operations such as open wound therapy and steel plate fixation or the like, such that the reduction condition may be stably maintained until internal fixation is completed.

INDUSTRIAL APPLICABILITY

During operation with the three-dimensional repositor for claviclar fracture of the present disclosure, the patient is allowed to lie on her or his back, locating the locating holes at the supporting rods corresponding to two ends of the fractured clavicle respectively, fixing the locating hole by locating screw, then the dislocated clavicle could be moved upwards, downwards, leftwards or rightwards to be respited with the cooperation of the cross bar of the first reduction device and a plurality of Kirschner wires. Further, if the second reduction device is provided, pulling the clavicle with longitudinal dislocation sideward by the second reduction device, then passing the Kirschner wire through the reduction hole of the cross bar to press or raise the fractured clavicle. The distance between two ends of the pulled clavicle could be controlled by the second reduction device, and maintained to reach a stable reduction condition by cooperation of the second reduction device and screw at the cross bar until internal fixation is completed. The present disclosure is smartly designed with simple structure, convenient to use, thus the effect of stable three-dimensional reduction for the claviclar fracture is achieved, which relieves patient's pain and reduces difficulty for operation, produces unexpected technical effect. The present disclosure is welcomed by medical staff and patient, and is worthy of popularization.

Exemplary embodiments have been specifically shown and described as above. It is to be understood that both the foregoing general description are exemplary and explanatory only and are not restrictive of the invention. It will be appreciated the aforesaid embodiments may be modified and portions of the technical features therein may be equally changed, which does not depart from the spirit or principle. All suitable modifications and equivalent which come within the spirit and scope of the appended claims are intended to fall within the scope of the disclosure.

What is claimed is:

1. A three dimensional repositor for claviclar fracture, wherein the three-dimensional repositor comprising:

two supporting rods pivotally cross-connected to each other, forming an X-shape, by a rotation shaft extending therethrough, each of said two supporting rods comprises a distal straight part, an intermediate curved part and a proximal extension rod, and said rotation shaft extends through two ends of the curved parts of said two supporting rod, such that the distal straight parts and the intermediate curved parts are located on a distal side of the rotation shaft and the proximal extension rods are located on an opposite proximal side of the rotation shaft; each of the supporting rods has a position block connected to the distal straight part by at least one lockably universal wheel joint disposed at one or both of distal and proximal sides of the position block, said position block has a top side, an opposite bottom side and a locating hole extending through the top and bottom sides perpendicular to at the distal straight part in a first configuration, each of said locating holes has a diameter matching with a diameter of either a locating screw or a Kirschner wire the distal straight part of each of the two support rods includes two straight portions rotatably joined to the position block by the at least one lockably universal wheel joint, such that a distal one of the straight portions, rotatably joined to the distal side of the position block with the at least one lockably universal wheel joint, rotates relative to a proximal one of the straight portions joined to the proximal side of the position block about at least one axis of the lockably universal wheel joint to position and lock the straight portions at a range of desired angles relative to one another;

one of the proximal extension rods includes a screw rod, and the other of the proximal extension rods includes a screw hole matching the screw rod; and wherein rotation of the screw rod in the screw hole changes a distance between the distal straight parts of the support rods; and at least one reduction device connected to the distal straight portions of the distal straight part of the support rods the at least one reduction device comprising:

two pillars, each of the pillars extends along a longitudinal axis between a top end and a bottom end connected to the distal straight portion of the straight part of a corresponding one of the two supporting rods, such that each of the pillars extends perpendicularly to the distal straight portion of the straight part of a corresponding one of the two supporting rods; and an elongated cross bar rotatably connected to the top ends of the two pillars, such that the cross bar extends perpendicularly to the two pillars and the distal straight portions of the distal straight parts of the two support rods, wherein a rotation hole or a chip is provided at the top end of each of the two pillar, and a rotation shaft projects outwardly from each of opposite longitudinal ends of the elongated cross bar and passes through a corresponding one of the rotation hole of the pillar or is received in the chip of the pillar, and said cross bar includes a plurality of reduction holes extending therethrough at different orientations from one another and having a diameter matching with the diameter of the Kirschner wire.

2. The three-dimensional repositor for claviclar fracture according to claim 1, wherein a screw hole extends through the cross bar and communicates with the reduction hole, in which a screw is received for tightly pressing the Kirschner wire.

3. The three-dimensional repositor for claviclar fracture according to claim 1, wherein upper surfaces of the straight parts of the two supporting rods are disposed in a same plane.

\* \* \* \* \*